Figure 1:
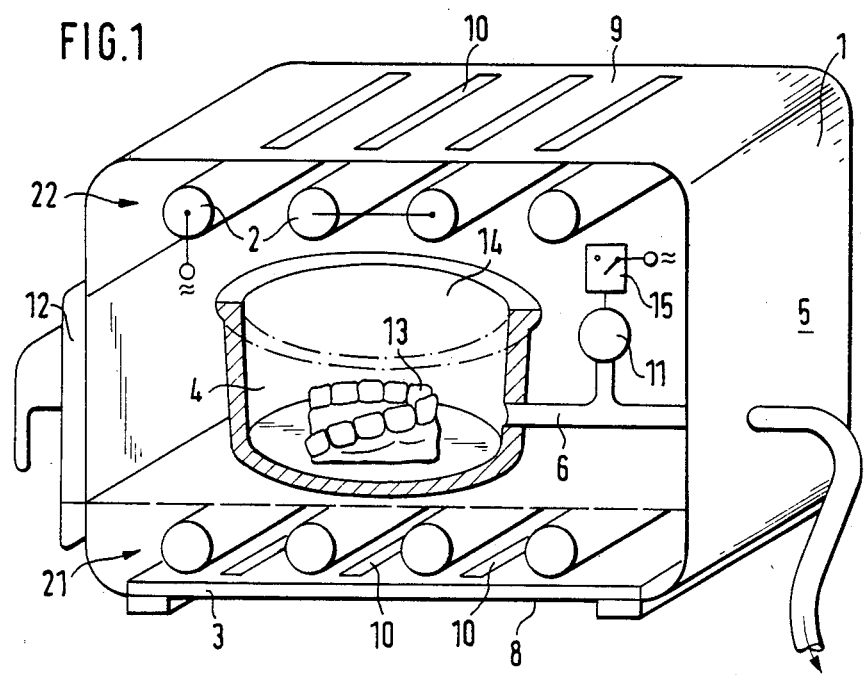

United States Patent [19]

Herold et al.

[11] Patent Number: 4,571,665

[45] Date of Patent: Feb. 18, 1986

[54] APPARATUS FOR TREATING DENTAL MATERIALS

[75] Inventors: Wolf-Dietrich Herold, Hechendorf; Karl L. Grafwallner, Munich; Michael Keller, Lochham, all of Fed. Rep. of Germany

[73] Assignee: ESPE Fabrik pharmazeutischer Praeparate GmbH, Fed. Rep. of Germany

[21] Appl. No.: 474,263

[22] Filed: Mar. 11, 1983

[30] Foreign Application Priority Data

Apr. 2, 1982 [DE] Fed. Rep. of Germany ....... 3212379

[51] Int. Cl.$^4$ ............................. F21S 3/00; A61N 5/00
[52] U.S. Cl. ..................................... 362/225; 128/396; 250/492.1; 362/216; 362/217; 362/230; 362/247; 362/255; 362/260; 362/276; 362/293; 362/802; 362/804; 433/215
[58] Field of Search .............. 362/804, 260, 257, 154, 362/216, 230, 225, 217, 247, 276, 255, 293, 804, 802; 422/186.3; 128/13, 22, 23, 395, 396; 206/368; 433/29, 30, 31, 215, 217

[56] References Cited

U.S. PATENT DOCUMENTS

| | | | |
|---|---|---|---|
| 3,643,078 | 2/1972 | Lewis | 362/216 |
| 3,704,928 | 12/1972 | Coombs et al. | 350/1 |
| 3,938,132 | 2/1976 | Cunningham | 362/154 |
| 3,974,584 | 8/1976 | Shorette | 362/216 |
| 4,071,424 | 1/1978 | Dart et al. | 204/159.23 |
| 4,089,763 | 5/1978 | Dart et al. | 204/159.25 |
| 4,122,349 | 10/1978 | Fouassier et al. | 252/301.4 F |
| 4,184,196 | 1/1980 | Moret et al. | 362/804 |
| 4,195,329 | 3/1980 | Woog | 362/804 |
| 4,237,027 | 12/1980 | Dougler et al. | 252/301.4 H |
| 4,254,454 | 3/1981 | Hardin, Jr. | 362/804 |
| 4,254,455 | 3/1981 | Neal, Jr. | 362/804 |
| 4,266,535 | 5/1981 | Moret | 362/804 |
| 4,280,167 | 7/1981 | Ellett | 362/304 |
| 4,292,664 | 9/1981 | Mack | 362/205 |
| 4,344,115 | 8/1982 | Pickens et al. | 362/216 |
| 4,349,864 | 9/1982 | Smith | 362/154 |
| 4,385,344 | 5/1983 | Gonser | 362/32 |

FOREIGN PATENT DOCUMENTS

| | | |
|---|---|---|
| 827554 | 7/1949 | Fed. Rep. of Germany . |
| 2523587 | 5/1975 | Fed. Rep. of Germany . |
| 3207637 | 3/1982 | Fed. Rep. of Germany . |

OTHER PUBLICATIONS

"Der Präparator", 1975, vol. 19, pp. 99 to 106, and vol. 21, pp. 5 to 7.
"Plexit 55", advertising material of the company Röhm, (Apr. 1981).
"Speziallampen für Erstbestückung", advertising material of the company Philips, published May 1980.
"Chemie in Unserer Zeit", vol. 13, No. 5, Oct. 1979, pp. 142 to 146.

Primary Examiner—Stephen J. Lechert, Jr.
Assistant Examiner—Howard J. Locker
Attorney, Agent, or Firm—Barnes & Thornburg

[57] ABSTRACT

In an apparatus for treating dental materials with radiation of a selected spectral range, a receptacle accommodating the material to be treated is surrounded by one or a plurality of fluorescent tubes. The maximum emission of the fluorescent tubes is about 460 nm. The receptacle which accommodates the dental material during the irradiation process is preferably hermetically sealed and is made of a material that is transparent to the radiation.

17 Claims, 3 Drawing Figures

APPARATUS FOR TREATING DENTAL MATERIALS

DESCRIPTION

The invention relates to an apparatus for treating dental materials.

For making dental prosthetic appliances such as crowns, single teeth, bridges, partial or total dentures, dental materials are used in the dental technical field which may be polymerized and cured with light by means of a photo-initiator system.

Due to the inherent colour of the polymerization initiators contained therein, these materials exhibit an undesired yellowish tinge which, however, may be permanently bleached out by a subsequent irradiation step to a shade of colour corresponding to the natural colour of teeth by causing an irreversible reaction. Typically, radiation in a range of about 400 nm to about 500 nm (the maximum being about 460 nm) is required for this bleaching-out operation, wherein the irradiation has to be effected for a major period of time of e.g. 30 minutes. At the same time this irradiation results in a desired further polymerization of the material.

Exposure devices have been developed for the curing step which use halogen-quartz lamps as the light source. Such exposure devices are described, for instance, in German Offenlegungsschrift No. 2,901,534 and European Patent Application, Publication No. 0037,461. These exposure devices produce a considerable quantity of heat which will heat the denture during the exposure time required for the curing to take place. Such an increase in temperature has a detrimental effect because the coefficient of thermal expansion of the synthetic resins used differs from that of, for instance, the metallic crowns which are to be faced with the synthetic resin. Therefore there is a tendency for thermal stresses to occur at the end of the curing process during cooling, which may possibly cause cracks and gaps at the interface between synthetic resin and metal; also, the synthetic resin itself may be subject to crack formation.

Although the thermal radiation has been reduced in the known apparatus by a special coating of the reflector of the light source as well as by the use of filters and cooling fans, a further decrease of the thermal radiation directed towards the parts to be treated is still desirable.

Furthermore it has been found to be a drawback of the known apparatus that the source of light, which is a point light source with an associated parabolic mirror, illuminates the objects substantially with a parallel beam. Accordingly, particularly in the case of arcuate dentures vignetting of some areas may occur so that in the vignetted areas the synthetic resin composition is either not, or but incompletely, cured and bleached out. This effect is also detrimental with respect to the adhesive power between a synthetic resin coating and a metallic surface, e.g. a metallic bridge structure. Small metal beads are sintered onto the surface of the metallic parts such that the metallic surface becomes uneven and small undercut regions are formed between the beads and the metallic surface into which regions the still liquid synthetic resin will penetrate upon application thereof. When the synthetic resin has been cured, these metallic beads acts as anchoring means for the entire resin coating. However, this anchoring effect will be lost if due to vignetting the light cannot penetrate into the undercut regions and the synthetic resin therein either cannot, or can but insufficiently, be cured.

Furthermore it is a source of error in the known apparatus that an operator may inadvertently insert the workpiece to be treated upside down, such that the synthetic resin which is to be cured and bleached out rests on the side which is facing away from the illuminating means.

For these reasons it is a further requirement for irradiating apparatus of the specified kind that the articles to be treated should as far as possible be illuminated uniformly and from all sides.

It is therefore the object of the present invention to devise an apparatus for treating dental materials in such a way that the radiation used for curing and bleaching-out will not heat the material and will strike the workpiece to be treated as uniformly as possible and from all sides.

This object is solved by an apparatus for treating dental materials with radiation of a selected spectral range, comprising a housing in which there are disposed: means for receiving the dental materials to be treated, at least one flourescent tube emitting radiation of said selected spectral range and disposed to surround said receiving means, and mirror means for reflecting radiation of said fluorescent tube towards said dental materials.

In accordance with the invention the light source to be used for exposure with the polymerization-initiating light consists of fluorescent tubes. Firstly, such fluorescent tubes exhibit low generation of heat, and secondly they are not point-like but the emission of light is areal so that the light emitted thereby does not have a privileged direction but is distributed diffusely. Thus there results a uniform irradiation of the area provided for accommodating a denture member. The means receiving the dental materials is surrounded by the fluorescent tube(s) used for illumination. If only a single fluorescent tube is used, this will have a spatial, e.g. helical, configuration such that light will be emitted from all sides towards the dental materials resting in the interior of the helix. Preferably, two rows of such fluorescent tubes are provided, for instance at the bottom and the top or roof of the apparatus, with the denture being disposed therebetween.

While it is known from U.S. Pat. No. 3,433,949 to perform a radiation treatment by using fluorescent tubes, that prior art specification is related to testing of chemicals for their radiant energy stability where an irradiation from all sides is of no relevance, in contrast to the bleaching and polymerisation of dental materials according to the present invention.

In the apparatus of the invention, the walls of the housing may additionally be provided with mirrors or reflectors so that the light will be incident from all sides on the dental materials to be treated.

The overall intensity emitted by the fluorescent tubes determines the required exposure time. Normally, this time is previously fixed. The fluorescent tubes are connected in series so as to ensure that during an irradiation process the emitted light intensity will not decrease due to an unnoticed failure of any individual fluorescent tubes, so that the overall intensity required for curing cannot be achieved. In that case failure of a single fluorescent tube will result in the failure of all fluorescent tubes, such that the defective operation of the apparatus may be recognized.

The usual single-component materials which may be cured with visible light include a sensitizer which is stimulated by light having a wavelength of about 460 nm. Accordingly, it is preferred to use fluorescent tubes with a maximum emission of from between 400 and 500 nm, especially of about 460 nm. Such an emission may be achieved with fluorescent tubes which preferably have a europium-doped barium magnesium aluminate coating.

When, as is described in the above European Publication No. 0037,461, a single-component material is cured by means of light, a greasy layer will form on the surface of the material if oxygen is present in the ambient atmosphere, because oxygen molecules inhibit the polymerization. This incompletely cured layer leads under oral conditions to microcracks in the surface, resulting in discoloration. To overcome this difficulty, the denture has until now been placed in an interiorly metallized metal container which was covered by a glass plate and was evacuated prior to the exposure. However, in this apparatus the metallization will become somewhat dull in the course of time, because due to the action of the light the vapours from the single-component material will react on the surface of the metallized layer and form a deposit. It is hard to remove this deposit, and such removal may frequently result in the reflector becoming scratched or dull. In order to eliminate this difficulty it is provided in accordance with a further, especially preferred embodiment of the invention that a container is used which is adapted to be hermetically sealed and which consists of a material transparent to the respective required light, in particular a container made of glass or quartz. This container may be removed from the apparatus housing so that it may easily by wiped out and cleaned. In addition it is prevented that a dental prosthetic appliance positioned adjacent to the wall is cured uncompletely due to its own shadow.

Another embodiment of the afore-mentioned apparatus according to the invention has been further developed to the effect that a vacuum gauge is connected to the vacuum fitting and controls the activation and deactivation of the fluorescent tubes via a switch. Thus, the fluorescent tubes will only be activated when less than a predetermined pressure in the container interior and thus less than a critical oxygen content has been reached. If due to external influences the hermetic condition of the container deteriorates during exposure and air leaks into the container, the radiation will be deactivated and the operator will be informed of the malfunction by means of a signal.

In a further embodiment the container is provided with two gas fittings so that the oxygen may be displaced by a flow of gas, e.g. a flow of nitrogen or of argon. Control of the flow of gas may be effected by means of a flow meter.

Figure 3:
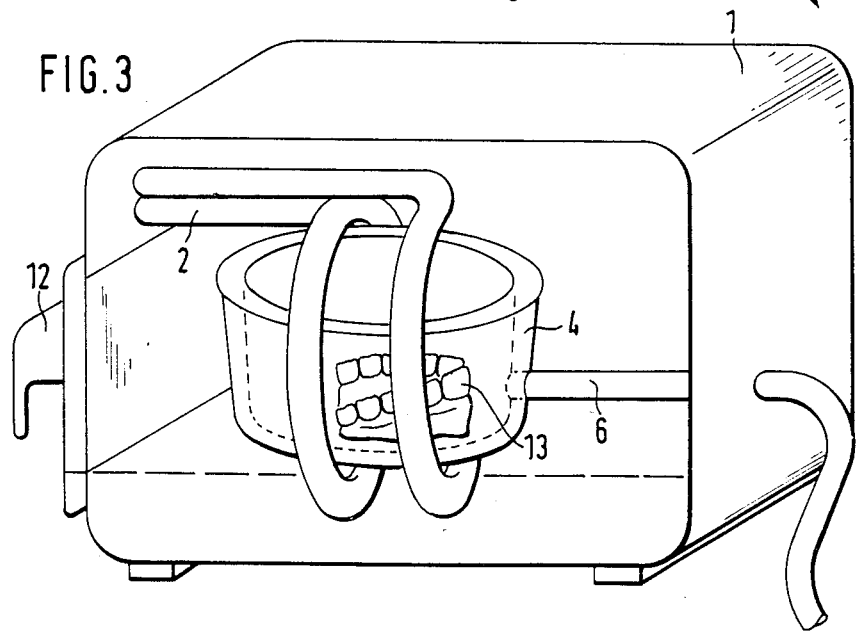
Figure 2:
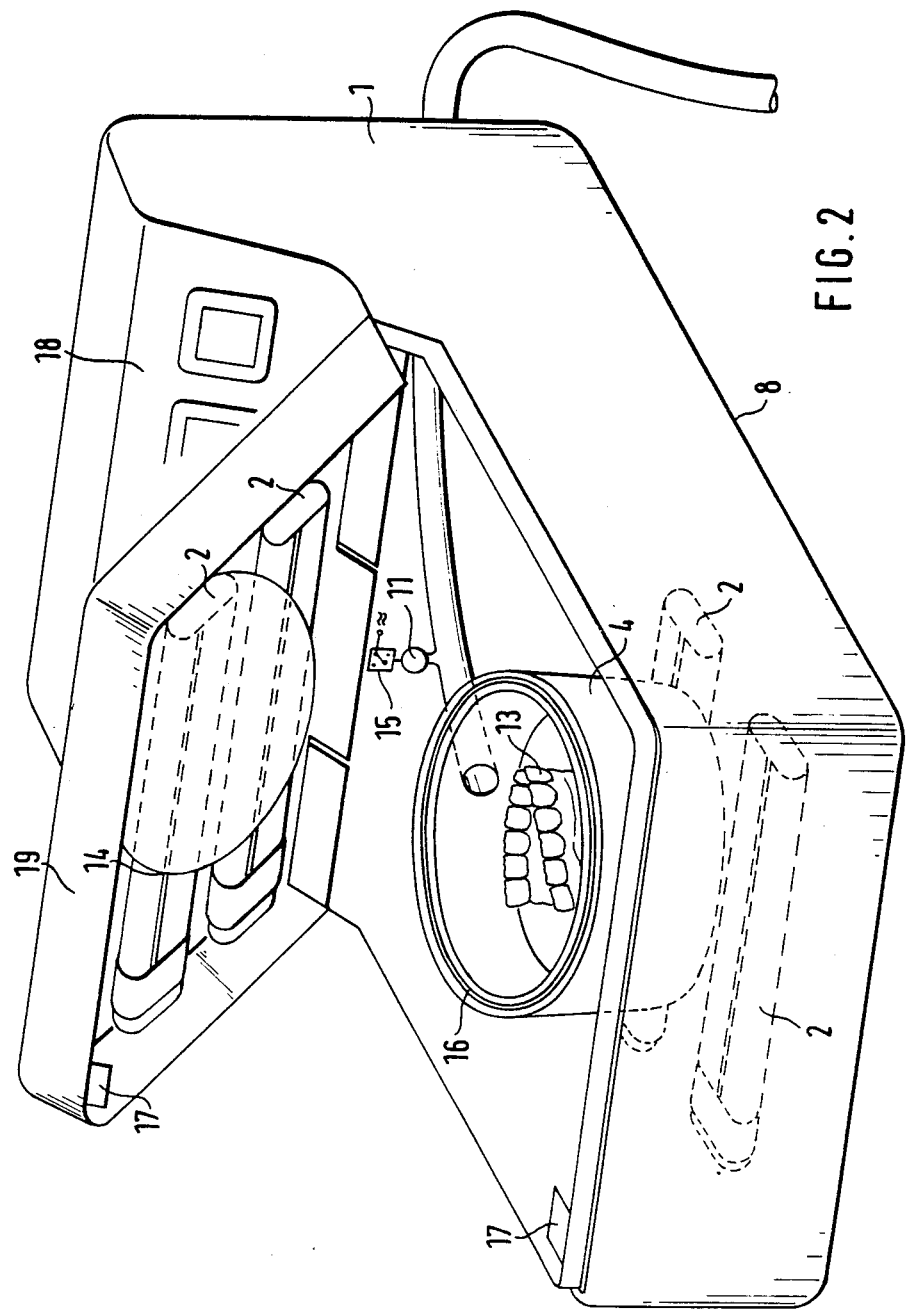

The invention will be described and explained in detail with reference to the embodiments shown in the drawings, in which:

FIG. 1 shows schematically a first embodiment of the apparatus according to the invention, FIGS. 2 and 3 show further embodiments of the invention.

In the embodiment according to FIG. 1 a row of fluorescent tubes 21 and 22 is provided inside a housing 1 on the inside of the bottom 8 and the top 9, respectively. Said fluorescent tubes are coated with a europium-doped barium magnesium aluminate such that the fluorescent lamps exhibit their maximum emission in a spectral region of about 460 nm. The sensitizer, which is added to the single-component material and causes polymerization will be activated and bleached-out by light of this wavelength.

For better utilization of the light emitted by the fluorescent tubes 2 reflectors 3 are disposed on the inside of the housing, which have a high reflection coefficient in the selected spectral region. Instead of such reflectors it would also be possible to provide the corresponding inner surfaces of the bottom 8, the top 9 and the sidewalls 5 with a reflective coating, e.g. of aluminium or chromium. Instead of such reflectors provided on the walls there might also be provided an interiorly metallized cylinder with an open end face and having the receptacle disposed in the interior thereof. It is particularly advantageous to deposit the reflective coating directly on the exterior of the receptacle 4 as this will prevent the reflector from becoming dull due to dirt, scratches or the like.

The container-like receptacle 4 for the denture 13 is disposed between the two rows 21 and 22 of fluorescent tubes 2. Said receptable 4 consists of a material which is transparent at the desired spectral region. For a spectral region of 460 nm the appropriate materials are glass and quartz. In the present embodiment the receptacle 4 is provided with a vacuum fitting 6. The denture 13 to be treated is placed inside the receptacle 4, whereupon the cover 14, which is sealed by a flexible sealing element, is placed thereon and the receptacle 4 is evacuated. A vacuum gauge 11 is connected to the vacuum fitting 6 and controls a switch 15. The supply voltage is applied to the fluorescent tubes 2 through the switch 15. When the receptacle 4 has reached a predetermined minimum vacuum (e.g. 5 mbar), the vacuum gauge 11 will become operative and close the switch 15, so that the supply voltage is applied to the fluorescent tubes and the irradiation will be initiated.

In the embodiment shown, the receptacle 4 accommodating the denture 13 may be removed from the housing 1, e.g. for cleaning purposes, by means of a drawer 12.

FIG. 2 shows another embodiment, in which the housing 1 is opened by means of a hinged top 19. Both the hinged top 19 and the bottom 8 are provided with two fluorescent tubes 2. These fluorescent tubes are modified relative to the embodiment of FIG. 1 in that they are U-shaped so that they are relatively short while still emitting a large quantity of light.

In this second embodiment the cover 14 is preferably mounted within the hinged top 19, in particular it is suspended therein by one or several springs. When the hinged top 19 is closed the cover 14 will be urged by the action of the springs onto the sealing member 16 of the receptacle 4 so that the latter will be positively closed. A solenoid 17 provides for complete closing of the hinged top and thus of the receptacle 4 and subsequently actuates a vacuum pump (not shown), e.g. through a switch. When the predetermined vacuum has been reached, the fluorescent tubes 2 will be activated for a preset period of time by the switch 15, which is controlled by the vacuumm gauge 11. When the sealing is insufficient, or when the preset vacuum is not reached within a predetermined time, an error indication will be displayed on the display panel 18 of the apparatus, and possibly an acoustic signal will also be generated.

FIG. 3 shows an alternative of the apparatus according to FIG. 1. Instead of two rows of fluorescent tubes only a single fluorescent tube is provided, which is helically disposed around the receptacle 4. By means of the drawer 12 the receptacle 4 may be moved into the interior of the helix, so that light will be uniformly directed from all sides onto the piece of material 13 disposed in the receptacle.

We claim:

1. Apparatus for curing dental prosthetic part means such as crowns, single teeth, bridges, dentures and the like made of photopolymerizable material, comprising:
   a housing,
   receiving means disposed in said housing for accomodating the prosthetic part means to be treated,
   at least one fluorescent tube disposed in said housing for emitting radiation in the spectral range of 400 to 500 nm to cure the prosthetic part means disposed in the receiving means, said at least one fluorescent tube being disposed to surround the receiving means and irradiate said prosthetic part means to be treated, and
   mirror means disposed in said housing for reflecting radiation of said at least one fluorescent tube towards the prosthetic part means, said at least one fluorescent tube in combination with said mirror means being capable of irradiating said prosthetic part means uniformly from all sides.

2. The apparatus of claim 1, wherein said receiving means is surrounded by one fluorescent tube of spatial configuration.

3. The apparatus of claim 1, wherein a plurality of fluorescent tubes are disposed along each of two opposite walls of the housing.

4. The apparatus of claim 1, wherein said mirror means includes a reflector provided on at least one wall of said housing.

5. The apparatus of claim 1, wherein a plurality of said fluorescent tubes are connected in series.

6. The apparatus of claim 1, wherein the at least one fluorescent tube has its emission maximum in a spectral range between 400 and 500 nm, especially at about 460 nm.

7. The apparatus of claim 6, wherein said at least one fluorescent tube includes a europium-doped coating of a barium magnesium aluminate.

8. The apparatus of claim 1, wherein said receiving means includes a container adapted to be hermetically sealed and consisting of a material transparent to a preselected spectral region.

9. The apparatus of claim 8, wherein said container is made of glass.

10. The apparatus of claim 8, wherein said container is provided with a vacuum connection.

11. The apparatus of claim 8, wherein said container is provided with two gas connections.

12. The apparatus of claim 10, including a vacuum gauge which controls the activation and deactivation of at least one said fluorescent tube.

13. The apparatus of claim 1, wherein said receiving means is adapted to be removed from the housing.

14. The apparatus of claim 1, wherein said housing is formed with vent apertures in the bottom and the top thereof.

15. The apparatus of claim 1, wherein said mirror means includes reflecting surfaces surrounding said receiving means.

16. Apparatus according to claim 1, wherein said receiving means includes a hermetically sealable container for the prosthetic part means, said container being transparent to a preselected spectral range of the at least one fluorescent tube, and vacuum connection means for evacuating the container to facilitate treatment of the prosthetic part means by the radiation.

17. The apparatus of claim 1, further comprising door means for closing the housing during a curing operation.

* * * * *

UNITED STATES PATENT AND TRADEMARK OFFICE
CERTIFICATE OF CORRECTION

PATENT NO. : B1 4,571,665

DATED : April 19, 1988

INVENTOR(S) : Wolf-Dietrich Herold, et al

It is certified that error appears in the above-identified patent and that said Letters Patent is hereby corrected as shown below:

On the title page Item "(45)" should read
-- Certificate Issued    April 19, 1988 --.

Signed and Sealed this

Eighth Day of November, 1988

Attest:

DONALD J. QUIGG

*Attesting Officer*  *Commissioner of Patents and Trademarks*

REEXAMINATION CERTIFICATE (839th)
United States Patent [19]
Herold et al.

[11] B1 4,571,665
[45] Certificate Issued  Apr. 19, 1986

[54] APPARATUS FOR TREATING DENTAL MATERIALS

[75] Inventors: Wolf-Dietrich Herold, Hechendorf; Karl L. Grafwallner, Munich; Michael Keller, Lochham, all of Fed. Rep. of Germany

[73] Assignee: ESPE Fabrik pharmazeutischer Praeparate GmbH, Fed. Rep. of Germany

Reexamination Request:
No. 90/001,148, Dec. 30, 1986

Reexamination Certificate for:
Patent No.: 4,571,665
Issued: Feb. 18, 1986
Appl. No.: 474,263
Filed: Mar. 11, 1983

[30] Foreign Application Priority Data
Apr. 2, 1982 [DE] Fed. Rep. of Germany ....... 3212379

[51] Int. Cl.⁴ .............................. F21S 3/00; A61N 5/00
[52] U.S. Cl. .................................... 362/225; 128/396; 250/492.1; 362/216; 362/217; 362/230; 362/247; 362/255; 362/260; 362/276; 362/293; 362/802; 362/804; 433/215
[58] Field of Search ................ 362/260, 257, 154, 216, 362/230, 225, 217, 247, 276, 255, 293, 802, 804; 422/186.3; 128/13, 22, 23, 395, 396; 206/368; 433/29, 30, 31, 215, 217

[56] References Cited

U.S. PATENT DOCUMENTS

| | | | |
|---|---|---|---|
| 3,643,078 | 2/1972 | Lewis | 362/216 |
| 3,704,928 | 12/1972 | Coombs et al. | 350/1 |
| 3,938,132 | 2/1976 | Cunningham | 362/154 |
| 3,974,584 | 8/1976 | Shorette | 362/216 |
| 4,071,424 | 1/1978 | Dart et al. | 204/159.23 |
| 4,089,763 | 5/1978 | Dart et al. | 204/159.25 |
| 4,122,349 | 10/1978 | Fouassier et al. | 252/301.4 F |
| 4,184,196 | 1/1980 | Moret et al. | 362/804 |
| 4,195,329 | 3/1980 | Woog | 362/804 |
| 4,237,027 | 12/1980 | Dougler et al. | 252/301.4 H |
| 4,254,454 | 3/1981 | Hardin, Jr. | 362/804 |
| 4,254,455 | 3/1981 | Neal, Jr. | 362/804 |
| 4,266,535 | 5/1981 | Moret | 362/804 |
| 4,280,167 | 7/1981 | Ellett | 362/304 |
| 4,292,664 | 9/1981 | Mack | 362/205 |
| 4,344,115 | 8/1982 | Pickens et al. | 362/216 |
| 4,349,864 | 9/1982 | Smith | 362/154 |
| 4,385,344 | 5/1983 | Gonser | 362/32 |
| 4,412,134 | 10/1983 | Herold et al. | 250/504 R |

FOREIGN PATENT DOCUMENTS

| | | |
|---|---|---|
| 0037461 | 10/1981 | European Pat. Off. . |
| 0827554 | 7/1949 | Fed. Rep. of Germany . |
| 2523587 | 5/1975 | Fed. Rep. of Germany . |
| 8007265 | 8/1981 | Fed. Rep. of Germany . |
| 3207637 | 3/1982 | Fed. Rep. of Germany . |

OTHER PUBLICATIONS

"Chemie in Unserer Zeit", vol. 13, No. 5, Oct. 1979, pp. 142–146.
"Der Preparator" 1975, vol. 21, pp. 5–7 (Original and English translation).
English translation of p. 3 of EP #0037461.
"Der Preparator", 1975, vol. 19, pp. 99–106.
"Plexit 55", advertising material of the company Röhm, (Apr. 1981).

*Primary Examiner*—John F. Terapane

[57] ABSTRACT

In an apparatus for treating dental materials with radiation of a selected spectral range, a receptacle accommodating the material to be treated is surrounded by one or a plurality of fluorescent tubes. The maximum emission of the fluorescent tubes is about 460 nm. The receptacle which accommodates the dental material during the irradiation process is preferably hermetically sealed and is made of a material that is transparent to the radiation.

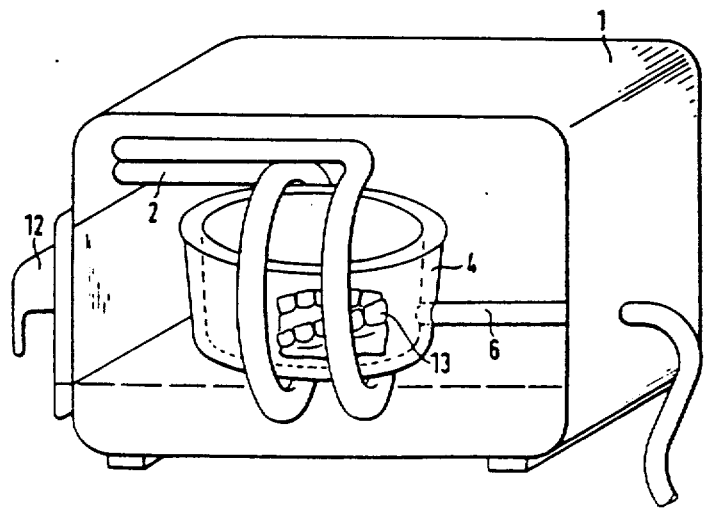

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1 and 3–17 is confirmed.

Claim 2 is determined to be patentable as amended.

New claims 18–36 are added and determined to be patentable.

2. The apparatus of claim 1, wherein said receiving means is surrounded by one fluorescent tube of [spatial] *spiral* configuration.

*18. Apparatus according to claim 1, wherein said mirror means includes reflection surface means disposed behind light emitting portions of the at least one fluorescent tube and facing the receiving means for reflecting light from said light emitting portions toward the receiving means.*

*19. Apparatus according to claim 18, wherein said at least one fluorescent tube comprises a plurality of said fluorescent tubes with at least one fluorescent tube disposed at each of respective different sides of the receiving means.*

*20. Apparatus according to claim 19, wherein said mirror means includes respective reflection surface means disposed behind respective light emitting portions of each of the fluorescent tubes and facing the receiving means for reflecting light from said respective light emitting portions toward the receiving means.*

*21. Apparatus according to claim 20, wherein said receiving means is a receptacle having a top facing at least one of the fluorescent tubes, a bottom facing at least one other of the fluorescent tubes, and side walls connecting the top and the bottom.*

*22. Apparatus according to claim 21, wherein said mirror means includes reflective surface means on said side walls.*

*23. Apparatus according to claim 21, wherein said side walls are cylindrical in shape.*

*24. Apparatus according to claim 21, wherein said top is a movable top which can be moved between an open position accomodating insertion and removal of dental parts and a closed position for accomodating curing operations.*

*25. Apparatus according to claim 24, wherein said top and said side walls are configured to hermetically seal the receptacle when in said closed position.*

*26. Apparatus according to claim 25, further comprising connection means opening to said receptacle for accomodating control of the gas content of the receptacle.*

*27. Apparatus according to claim 24, wherein said mirror means includes reflective surface means on said side walls.*

*28. Apparatus according to claim 24, wherein said top is hingedly connected to adjacent parts of the housing means.*

*29. Apparatus according to claim 27, wherein said receptacle is a glass container and said reflective surface means on said side walls includes a reflective coating on the outside of said side walls.*

*30. Apparatus according to claim 1, wherein said at least one fluorescent tube comprises a plurality of fluorescent tubes disposed at respective different sides of the housing.*

*31. Apparatus according to claim 30, wherein said respective different sides face one another, and wherein said receiving means is disposed between the fluorescent tubes.*

*32. Apparatus according to claim 1, comprising: vacuum connection means for evacuating an interior of said receiving means during curing operations to create a vacuum in said interior, vacuum gauge means for monitoring the vacuum in the said receiving means, and curing time control switch means controlled by the vacuum gauge means for activating the at least one fluorescent tube for a predetermined period of time when the vacuum gauge means detects a predetermined vacuum level.*

*33. Apparatus according to claim 32, wherein said mirror means includes reflection surface means disposed behind light emitting portions of the at least one fluorescent tube and facing the receiving means for reflecting light from said light emitting portions toward the receiving means.*

*34. Apparatus according to claim 33, wherein said at least one fluorescent tube comprises a plurality of said fluorescent tubes with at least one fluorescent tube disposed at a respective different side of the receiving means.*

*35. Apparatus according to claim 34, wherein said mirror means includes respective reflection surface means disposed behind respective light emitting portions of each of the fluorescent tubes and facing the receiving means for reflecting light from said respective light emitting portions toward the receiving means.*

*36. Apparatus according to claim 35, wherein said receiving means is a receptacle having a top facing at least one of the fluorescent tubes, a bottom facing at least one other of the fluorescent tubes, and side walls connecting the top and the bottom.*

* * * * *